US011250563B2

(12) United States Patent
Chen

(10) Patent No.: US 11,250,563 B2
(45) Date of Patent: Feb. 15, 2022

(54) HIERARCHICAL PROCESSING TECHNIQUE FOR LESION DETECTION, CLASSIFICATION, AND SEGMENTATION ON MICROSCOPY IMAGES

(71) Applicant: TENCENT AMERICA LLC, Palo Alto, CA (US)

(72) Inventor: Hanbo Chen, Seattle, WA (US)

(73) Assignee: TENCENT AMERICA LLC, Palo Alto, CA (US)

( * ) Notice: Subject to any disclaimer, the term of this patent is extended or adjusted under 35 U.S.C. 154(b) by 83 days.

(21) Appl. No.: 16/669,881

(22) Filed: Oct. 31, 2019

(65) Prior Publication Data

US 2021/0133956 A1 May 6, 2021

(51) Int. Cl.
G06T 7/00 (2017.01)
G06T 3/40 (2006.01)
G16H 30/40 (2018.01)
G16H 50/20 (2018.01)

(52) U.S. Cl.
CPC .............. *G06T 7/0012* (2013.01); *G06T 3/40* (2013.01); *G16H 30/40* (2018.01); *G16H 50/20* (2018.01); *G06T 2207/10056* (2013.01); *G06T 2207/20016* (2013.01); *G06T 2207/30024* (2013.01); *G06T 2207/30096* (2013.01)

(58) Field of Classification Search
CPC ......... G06T 7/0012; G06T 2207/10056; G06T 2207/20016; G06T 2207/30024; G06T 2207/30096; G16H 50/20; G16H 30/40
See application file for complete search history.

(56) References Cited

U.S. PATENT DOCUMENTS

| 6,018,728 A * | 1/2000 | Spence ................ G06K 9/3233 |
| | | 706/20 |
| 9,907,536 B2 * | 3/2018 | Courtney .............. A61M 5/007 |
| 10,910,099 B2 * | 2/2021 | Xu ............................ G06T 7/11 |
| 2006/0120608 A1 * | 6/2006 | Luo ...................... A61B 8/0825 |
| | | 382/224 |
| 2011/0243386 A1 * | 10/2011 | Sofka .................. G06K 9/6278 |
| | | 382/103 |

(Continued)

FOREIGN PATENT DOCUMENTS

| CA | 2 899 714 A | 9/2014 |
| WO | 2012061940 A1 | 5/2012 |

OTHER PUBLICATIONS

International Search Report dated Dec. 7, 2020 from the International Searching Authority in International Application No. PCT/US2020/047542.

(Continued)

*Primary Examiner* — Vu Le
*Assistant Examiner* — Julius Chai
(74) *Attorney, Agent, or Firm* — Sughrue Mion, PLLC

(57) ABSTRACT

A method and apparatus include performing a first image analysis at a first resolution of an input tissue image. An uncertainty map is generated based on performing the first image analysis. A set of uncertain regions of the input tissue image are identified based on the uncertainty map. A second image analysis of the set of uncertain regions is performed at a second resolution of the tissue image that is greater than the first resolution. An analysis result is generated based on the first image analysis and the second image analysis.

19 Claims, 8 Drawing Sheets

(56) References Cited

U.S. PATENT DOCUMENTS

2013/0113791 A1     5/2013   Issacs et al.
2017/0231550 A1*   8/2017   Do ...................... G06K 9/4652
                                                                                             382/128

OTHER PUBLICATIONS

Written Opinion dated Dec. 7, 2020 from the International Searching Authority in International Application No. PCT/US2020/047542.

* cited by examiner

HIERARCHICAL PROCESSING TECHNIQUE FOR LESION DETECTION, CLASSIFICATION, AND SEGMENTATION ON MICROSCOPY IMAGES

BACKGROUND

Different computer aided diagnosis (CAD) systems have been proposed so far to automatically or semi-automatically classify, detect, and segment lesions from microscopy images. Such systems can assist doctors and pathologists to increase their throughput and improve diagnosis quality. Some fully-automatic systems can also work alone to perform pre-diagnosis or offer a second opinion. A good CAD system can also reduce the cost, and, ultimately, can improve the wellness of patients.

Additional CAD systems are now integrating machine learning models such as convolutional neural networks (CNNs) or other deep learning methods. Machine learning models require large training. But once enough training data is provided, it can give expert level diagnosis or even outperform human experts. However, given the large size of images, computation on microscopy images with such system is time consuming and computationally expensive. Users may need to wait a long time to get results.

Notably, in some cases, doctors can quickly tell if a tissue is normal by looking at the overall appearance of the tissue in low resolution. For those samples, high resolution inspection is not necessary and can be avoided. In some other cases, when doctors cannot confidently make the decision or have suspect findings in coarse resolution, they will switch the zoom lens to zoom in to view the sample and inspect in more detail. A similar idea can be implemented by CAD systems to speed up the computation.

Moreover, current CAD systems designed for microscopy image analyze the images in a fixed high magnitude level. This will help maintain the detailed structure of tissues. However, when doctors inspect the abnormal tissue, they usually need to look at both the global appearance and the local cell shape to make the decision. Thus, by only processing images in high magnitude, the accuracy of current CAD systems could be limited.

SUMMARY

According to some possible implementations, a method may include performing a first image analysis at a first resolution of an input tissue image; generating an uncertainty map based on performing the first image analysis; identifying a set of uncertain regions of the input tissue image based on the uncertainty map; performing a second image analysis of the set of uncertain regions at a second resolution of the tissue image that is greater than the first resolution; and generating an analysis result based on the first image analysis and the second image analysis.

According to some possible implementations, a device comprises at least one memory configured to store program code; and at least one processor configured to read the program code and operate as instructed by the program code, the program code including: first performing code configured to cause the at least one processor to perform a first image analysis at a first resolution of an input tissue image; first generating code configured to cause the at least one processor to generate an uncertainty map based on performing the first image analysis; identifying code configured to cause the at least one processor to identify a set of uncertain regions of the input tissue image based on the uncertainty map; second performing code configured to cause the at least one processor to perform a second image analysis of the set of uncertain regions at a second resolution of the tissue image that is greater than the first resolution; and second generating code configured to cause the at least one processor to generate an analysis result based on the first image analysis and the second image analysis.

According to some possible implementations, a non-transitory computer-readable medium stores instructions, the instructions comprising: one or more instructions that, when executed by one or more processors of a device, cause the one or more processors to: perform a first image analysis at a first resolution of an input tissue image; generate an uncertainty map based on performing the first image analysis; identify a set of uncertain regions of the input tissue image based on the uncertainty map; perform a second image analysis of the set of uncertain regions at a second resolution of the tissue image that is greater than the first resolution; and generate an analysis result based on the first image analysis and the second image analysis.

DETAILED DESCRIPTION

The present disclosure provides a hierarchical image processing technique to speed up lesion detection on microscopy images. The system takes enlarged tissue images such as microscopy images (MSIs) (e.g., images acquired under microscopy) or whole-slide images (WSIs) (e.g., images acquired by a whole-slide imaging scanner) as input. It then automatically processes the images to identify lesions or abnormal tissues such as cancer cells on the image. The system can segment the lesion region and classify the lesion into subtypes. As compared to previous techniques, and to speed up computation, the system is configured to process images in a coarse level first. Based on determining that the coarse level is of low certainty, the system is configured to switch to a fine level. To improve prediction accuracy, the system is also configured to fuse information from different scales.

The present disclosure provides a hierarchical detection technique to efficiently and accurately detect tissue lesion from microscope images. This task has the following challenges which are addressed by the present disclosure: doctors need real-time response from the system, while large images with high resolution are difficult to be processed in real time. Some diagnoses can be confidently made in low magnitudes, and thus processing in high resolution is redundant. The present disclosure is configured to: $1^{st}$) inspect in low magnitude; $2^{nd}$) identify uncertain areas; $3^{rd}$) switch to higher magnitude to perform further analysis.

CNNs process the image based on local features which could be confusing for tissue images. The present disclosure provides a CNN that is configured to carry information from a lower magnitude to a higher magnitude when conducting computations.

Figure 1:
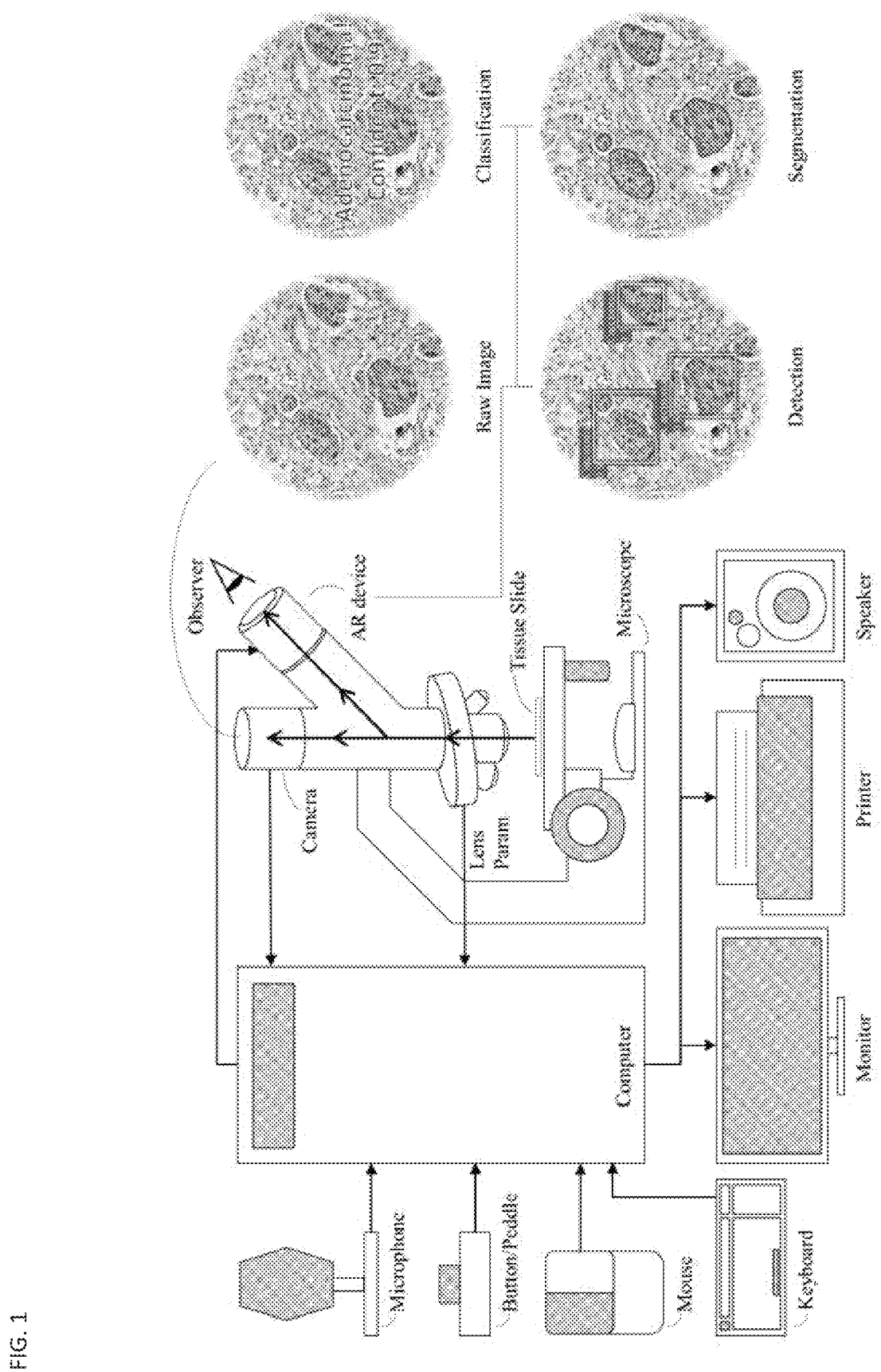
FIG. 1 is a diagram of an overview of an example implementation described herein.

As shown in FIG. 1, a camera may capture the view under a microscope. The computer may compute and generate the graphics based on the captured image. A user may observe the slide under a microscope. Feedback on the computation result may be stored and displayed on the computer monitor, displayed on an augmented reality (AR) monitor on the microscope, output via computer-generated speech, or printed on paper. The computation result may include, but is not limited to, classification (classify images into normal or lesion types), detection (detect the lesion site and classify each site), and segmentation (segment image into regions of different types).

As shown, the system of FIG. 1 is comprised of the following components implemented in hardware and/or software. The microscope is configured to zoom and inspect slide. The microscope may send a signal to the computer to instruct the computer which objective lens is currently in use when the objective lens is switched or the computer may send a request signal for the information. The digital camera may be installed on the lens tube to capture the view under microscope. The AR lens may be installed on the ocular to overlay the virtual screen on top of the view of slide.

The computer may be configured to perform image computation and data storage. The microphone may be configured to provide an voice input device for user to control the system, and may be configured for speech control of the system.

The monitor may be configured to display a result. The printer may be configured to print a result. The speaker may be configured to provide computer-generated speech. The button/paddle may be configured to control the system. The mouse/keyboard may be configured to provide a computer input device or peripheral device.

Figure 2:
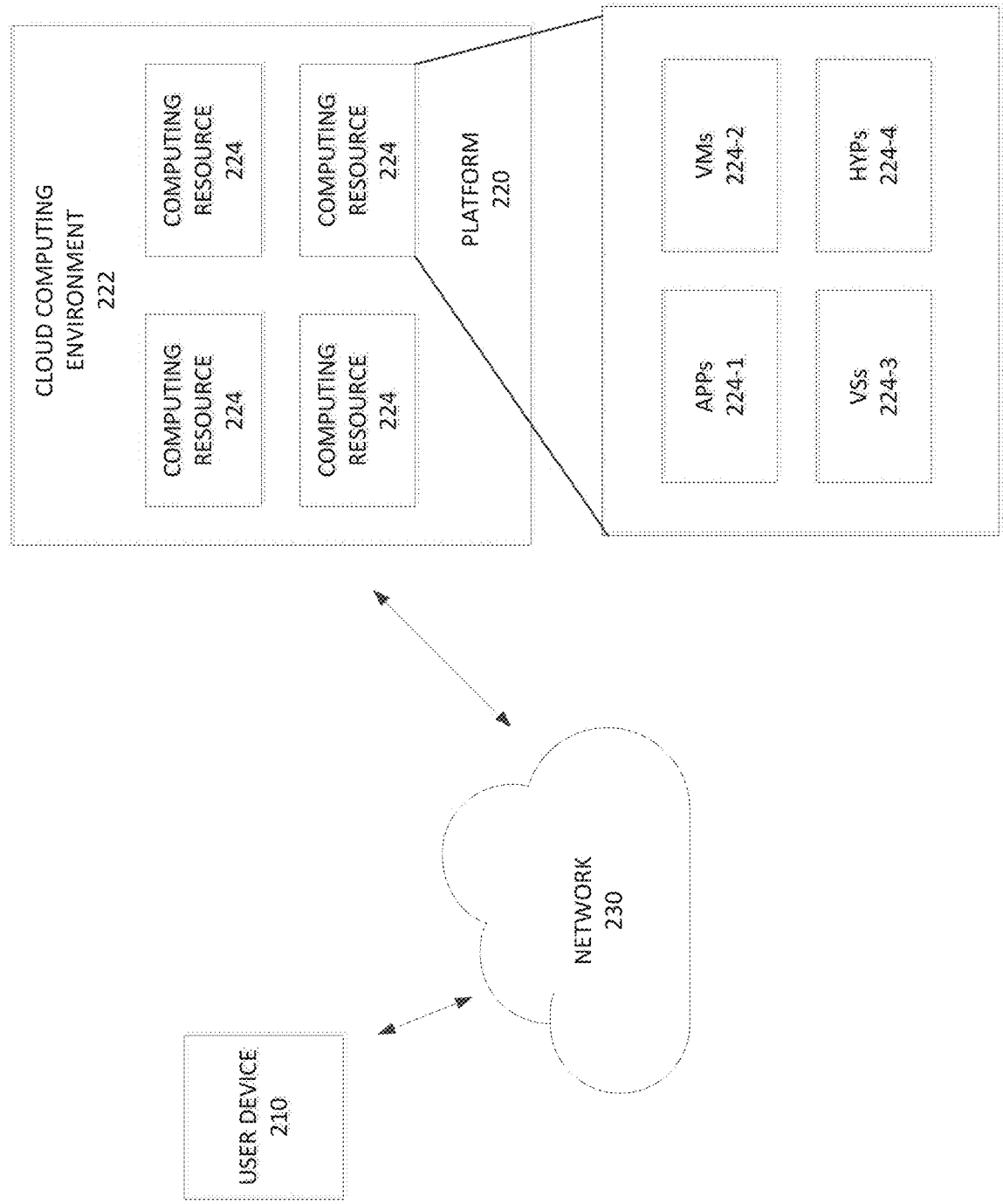
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include a user device 210, a platform 220, and a network 230. Devices of environment 200 may interconnect via wired connections, wireless connections, or a combination of wired and wireless connections.

User device 210 includes one or more devices capable of receiving, generating, storing, processing, and/or providing information associated with platform 220. For example, user device 210 may include a computing device (e.g., a desktop computer, a laptop computer, a tablet computer, a handheld computer, a smart speaker, a server, etc.), a mobile phone (e.g., a smart phone, a radiotelephone, etc.), a wearable device (e.g., a pair of smart glasses or a smart watch), or a similar device. In some implementations, user device 210 may receive information from and/or transmit information to platform 220.

Platform 220 includes one or more devices capable of performing hierarchical image processing, as described elsewhere herein. In some implementations, platform 220 may include a cloud server or a group of cloud servers. In some implementations, platform 220 may be designed to be modular such that certain software components may be swapped in or out depending on a particular need. As such, platform 220 may be easily and/or quickly reconfigured for different uses.

In some implementations, as shown, platform 220 may be hosted in cloud computing environment 222. Notably, while implementations described herein describe platform 220 as being hosted in cloud computing environment 222, in some implementations, platform 220 is not be cloud-based (i.e., may be implemented outside of a cloud computing environment) or may be partially cloud-based.

Cloud computing environment 222 includes an environment that hosts platform 220. Cloud computing environment 222 may provide computation, software, data access, storage, etc. services that do not require end-user (e.g., user device 210) knowledge of a physical location and configuration of system(s) and/or device(s) that hosts platform 220. As shown, cloud computing environment 222 may include a group of computing resources 224 (referred to collectively as "computing resources 224" and individually as "computing resource 224").

Computing resource 224 includes one or more personal computers, workstation computers, server devices, or other types of computation and/or communication devices. In some implementations, computing resource 224 may host platform 220. The cloud resources may include compute instances executing in computing resource 224, storage devices provided in computing resource 224, data transfer devices provided by computing resource 224, etc. In some implementations, computing resource 224 may communicate with other computing resources 224 via wired connections, wireless connections, or a combination of wired and wireless connections.

As further shown in FIG. 2, computing resource 224 includes a group of cloud resources, such as one or more applications ("APPs") 224-1, one or more virtual machines ("VMs") 224-2, virtualized storage ("VSs") 224-3, one or more hypervisors ("HYPs") 224-4, or the like.

Application 224-1 includes one or more software applications that may be provided to or accessed by user device 210 and/or sensor device 220. Application 224-1 may eliminate a need to install and execute the software applications on user device 210. For example, application 224-1 may include software associated with platform 220 and/or any other software capable of being provided via cloud computing environment 222. In some implementations, one application 224-1 may send/receive information to/from one or more other applications 224-1, via virtual machine 224-2.

Virtual machine 224-2 includes a software implementation of a machine (e.g., a computer) that executes programs like a physical machine. Virtual machine 224-2 may be either a system virtual machine or a process virtual machine, depending upon use and degree of correspondence to any real machine by virtual machine 224-2. A system virtual machine may provide a complete system platform that supports execution of a complete operating system ("OS"). A process virtual machine may execute a single program, and may support a single process. In some implementations, virtual machine 224-2 may execute on behalf of a user (e.g., user device 210), and may manage infrastructure of cloud computing environment 222, such as data management, synchronization, or long-duration data transfers.

Virtualized storage 224-3 includes one or more storage systems and/or one or more devices that use virtualization techniques within the storage systems or devices of computing resource 224. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 224-4 may provide hardware virtualization techniques that allow multiple operating systems (e.g., "guest operating systems") to execute concurrently on a host computer, such as computing resource 224. Hypervisor 224-4 may present a virtual operating platform to the guest operating systems, and may manage the execution of the guest operating systems. Multiple instances of a variety of operating systems may share virtualized hardware resources.

Network 230 includes one or more wired and/or wireless networks. For example, network 230 may include a cellular network (e.g., a fifth generation (5G) network, a long-term evolution (LTE) network, a third generation (3G) network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
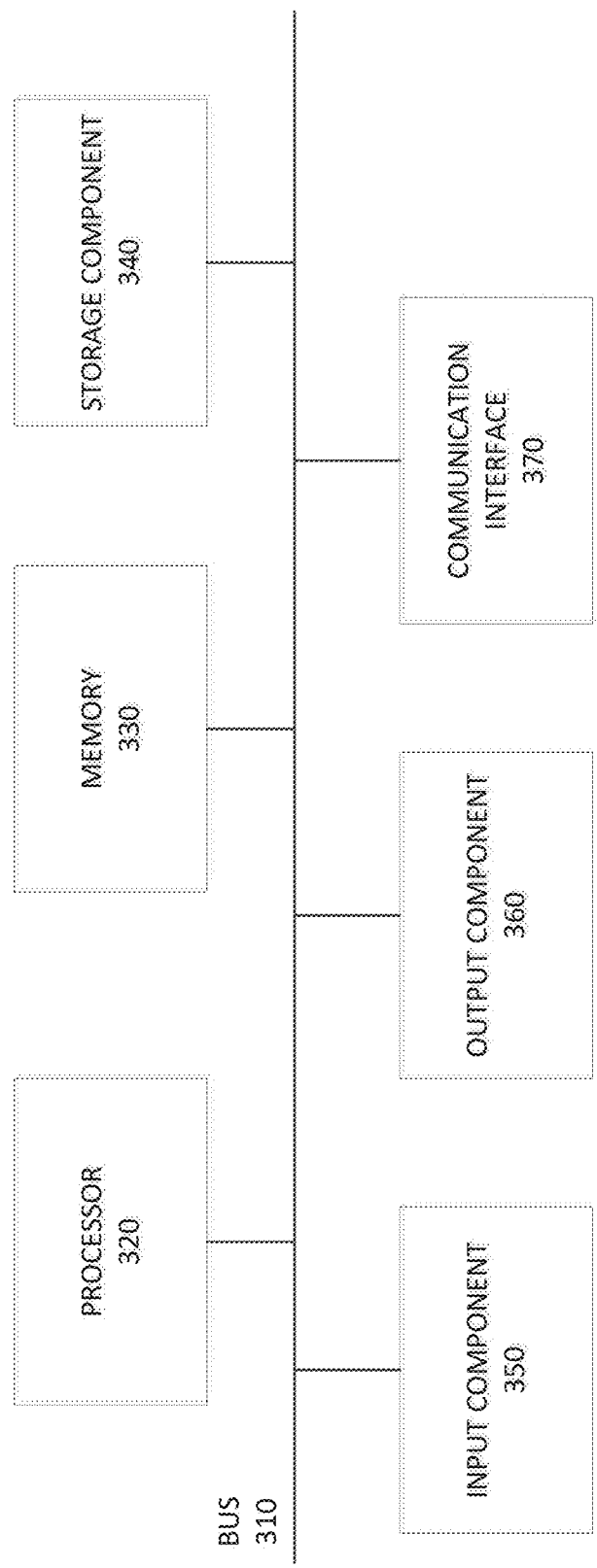
FIG. 3 is a diagram of example components of one or more devices of FIG. 2.

FIG. 3 is a diagram of example components of a device 300. Device 300 may correspond to user device 210 and/or platform 220. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
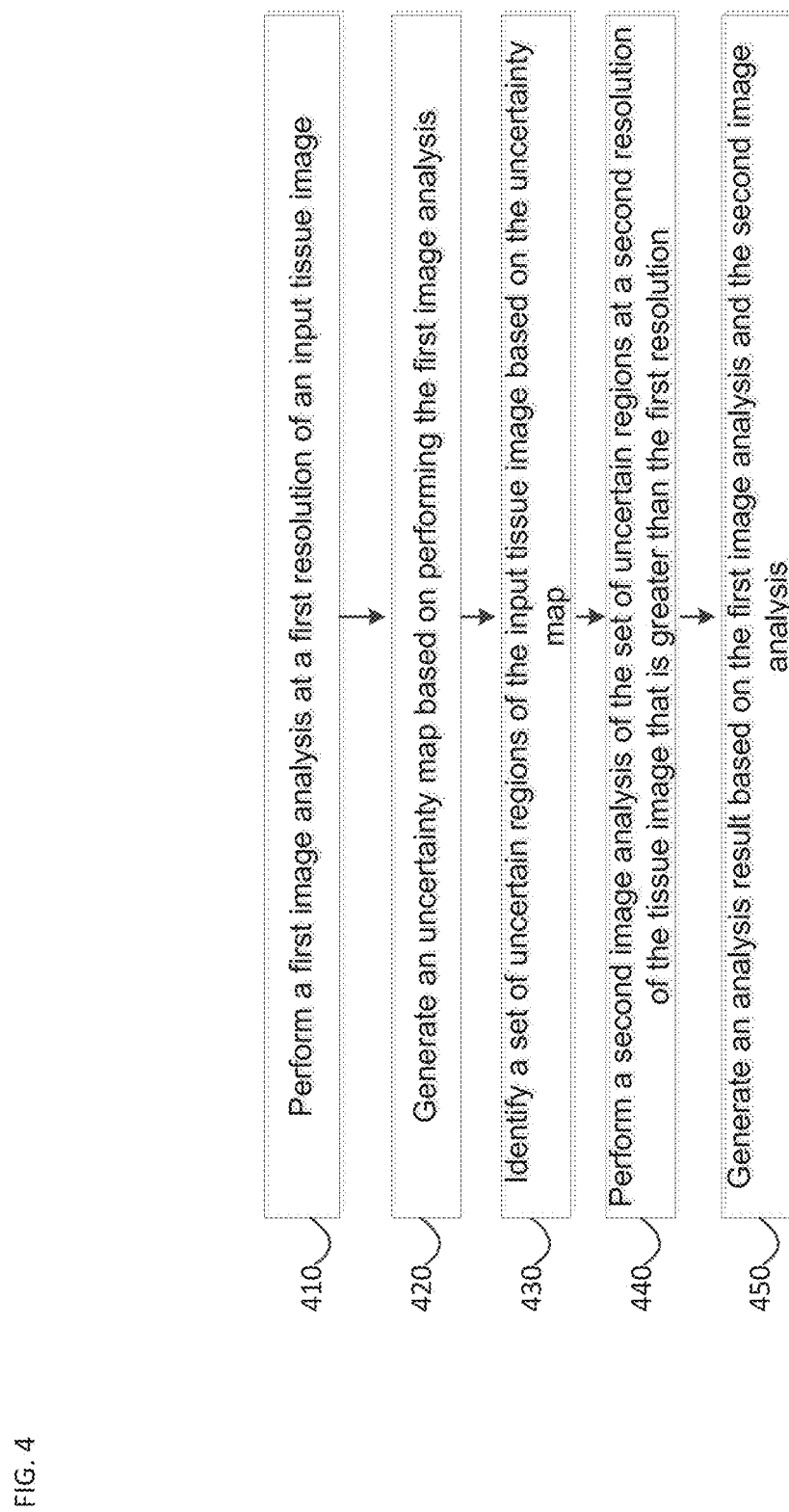
FIG. 4 is a flow chart of an example process for performing hierarchical image processing.

FIG. 4 is a flow chart of an example process 400 for performing hierarchical image processing. In some implementations, one or more process blocks of FIG. 4 may be performed by platform 220. In some implementations, one or more process blocks of FIG. 4 may be performed by another device or a group of devices separate from or including platform 220, such as user device 210.

As shown in FIG. 4, process 400 may include performing a first image analysis at a first resolution of an input tissue image (block 410).

As further shown in FIG. 4, process 400 may include generating an uncertainty map based on performing the first image analysis (block 420).

As further shown in FIG. 4, process 400 may include identifying a set of uncertain regions of the input tissue image based on the uncertainty map (block 430).

As further shown in FIG. 4, process 400 may include performing a second image analysis of the set of uncertain regions at a second resolution of the tissue image that is greater than the first resolution (block 440).

As further shown in FIG. 4, process 400 may include generating an analysis result based on the first image analysis and the second image analysis (block 450).

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

The foregoing disclosure provides illustration and description, but is not intended to be exhaustive or to limit the implementations to the precise form disclosed. Modifications and variations are possible in light of the above disclosure or may be acquired from practice of the implementations.

Figure 5:
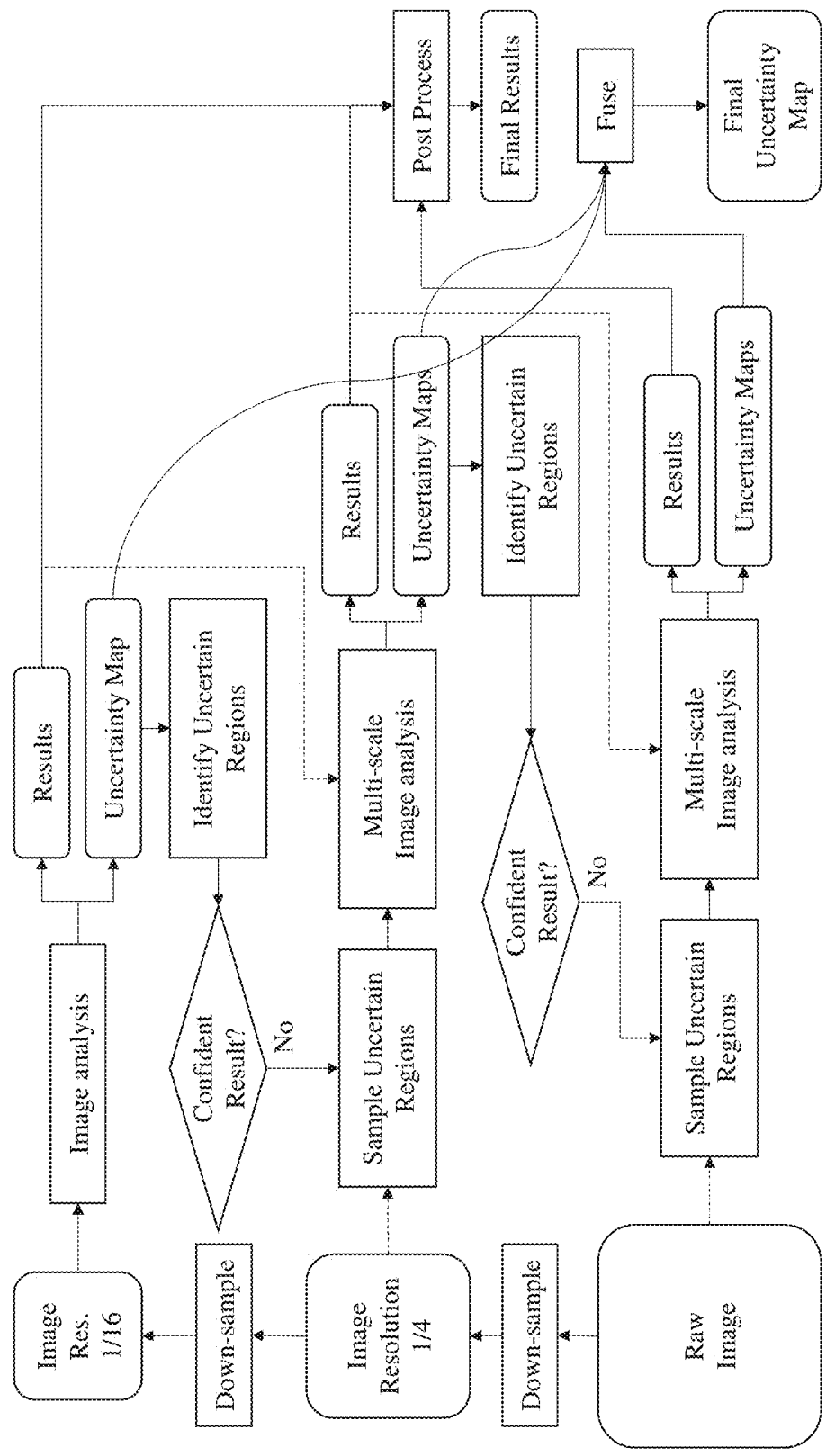
FIG. 5 is a diagram of a hierarchical processing system according to an embodiment.

FIG. 5 is a diagram of a hierarchical processing system according to an embodiment. Rectangular boxes indicate computation devices. Rounded corner rectangles indicate the input and output data of the computation devices. Arrows indicate data flow inside the system.

As shown in FIG. 5, a raw image is down-sampled into a lower resolution. The system may first process the lowest resolution (e.g., an image of a smallest size). After computation, results including classification, object detection, and segmentation are generated together with an uncertainty map. Based on the uncertainty map, uncertain regions may be identified. If there are uncertain regions, the image patches of uncertain regions in higher resolution may be computed. The system may iterate this process until a preset condition is satisfied (e.g., no further refinement is necessary, no uncertain regions are left, the highest resolution has been reached, etc.). The results and the uncertainty map generated in each resolution may be fused to generate the final results and the final uncertainty map.

Figure 6:
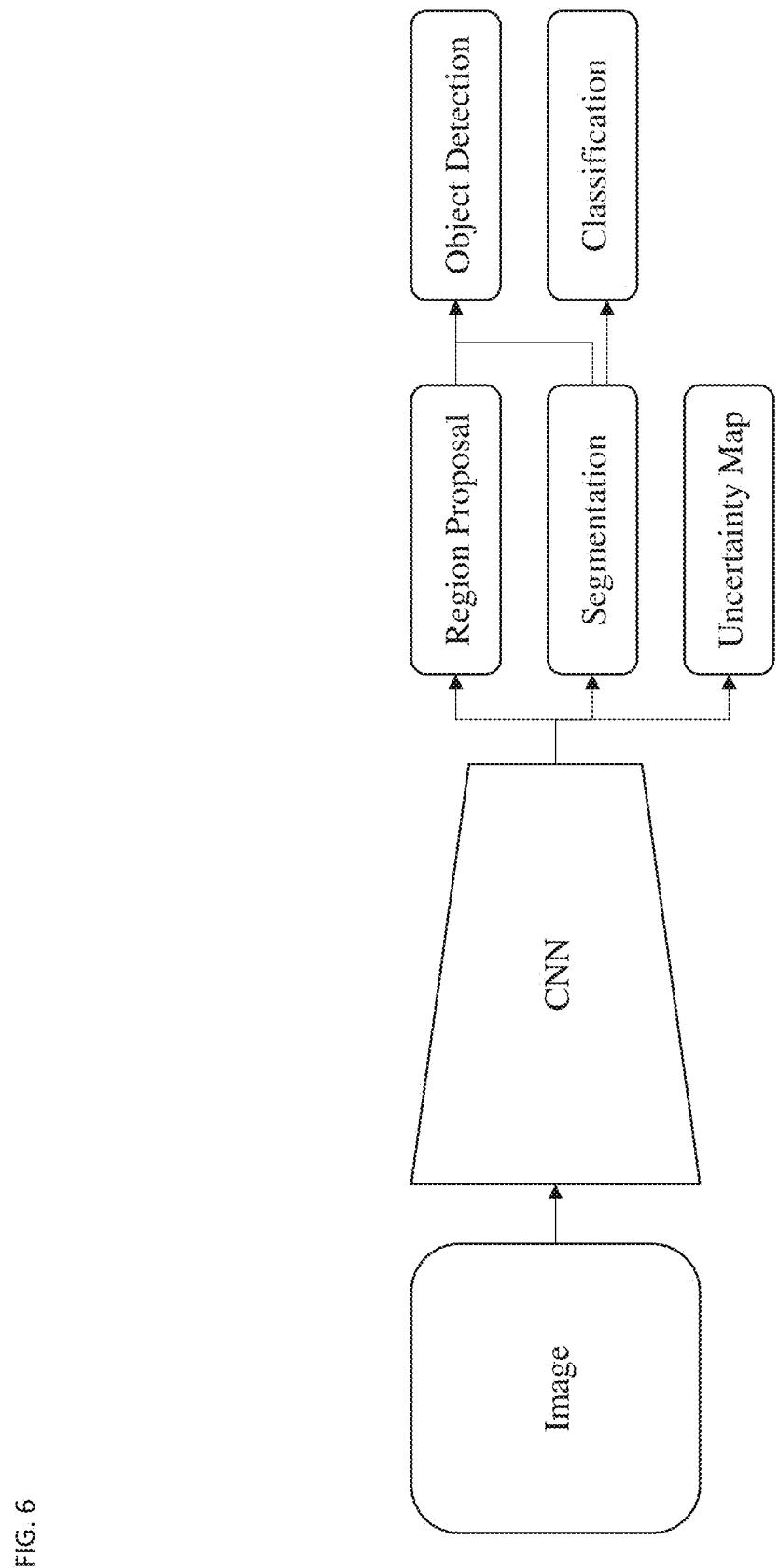
FIG. 6 is a diagram of an image analysis module according to an embodiment.

FIG. 6 is a diagram of an image analysis module according to an embodiment. The image analysis module can be implemented in different ways. FIG. 6 depicts a possible implementation of an image analysis module based on a CNN. A CNN is a deep learning technique. It is composed by a cascade of convolution layers, pooling layers, concatenation layers, deconvolution layers, normalization layers, etc. The output of one layer will be taken as input of the next layer. The CNN may be configured to directly generate region proposal, segmentation, and uncertainty maps. Segmentation classifies an image on a pixel-by-pixel basis. Region proposal indicates whether there is an object and the shape of the object. By voting based on a segmentation map, a classification result of the image can be generated. By voting inside each proposed region, object detection results of the image can be generated.

Figure 7:
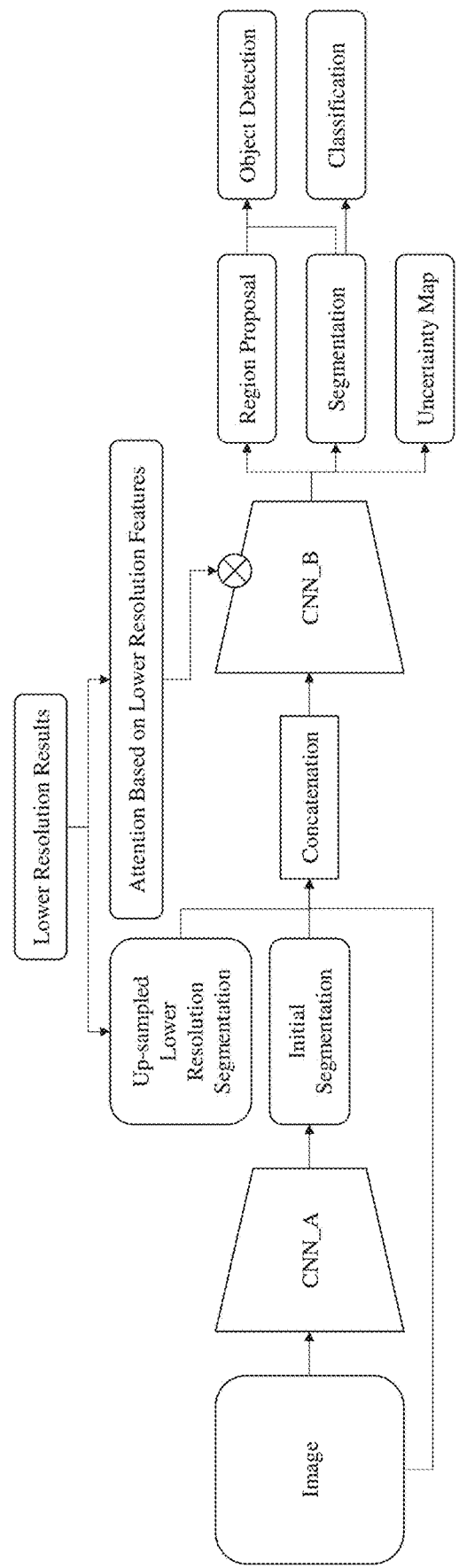
FIG. 7 is a diagram of a multi-scale analysis module according to an embodiment.

When jumping from lower resolution to higher resolution, computation results in lower resolutions can be fused via a multi-scale analysis module. This will help increase the receptive fields of the CNN in higher resolution and thus improve the accuracy of result. FIG. 7 depicts a possible implementation of multi-scale analysis module. An image may be first processed by a CNN to generate an initial segmentation. Then, the system may concatenate the initial segmentation with an up-sampled segmentation generated from a lower resolution and the input image for refinement. The concatenated matrix may be passed into another CNN to generate a final result. Inside this second CNN, the filters may be weighted by the attention generated based on lower resolution features.

Figure 8:
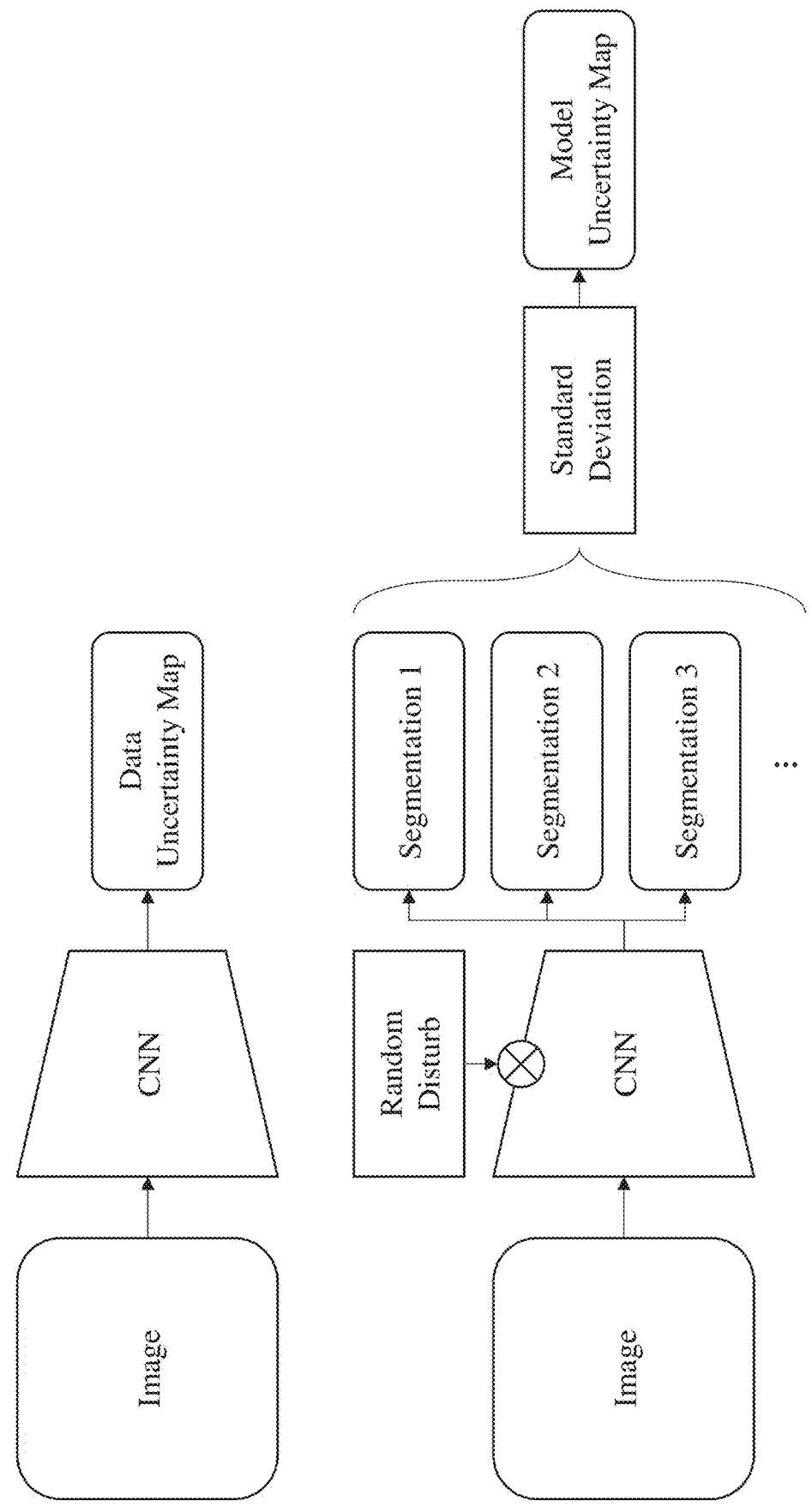
FIG. 8 is a diagram of computing uncertainty according to an embodiment.

There are different ways of computing uncertainty. Given a CNN model, an uncertainty map may be directly predicted by the CNN model (data uncertainty in FIG. 8), which may be similar to computing a segmentation map. The data uncertainty map includes the regions that the model is likely to make mistakes during training process. The system may also compute an uncertainty map by adding random disturbance inside the CNN model during prediction (model uncertainty in FIG. 8). With random disturbance, the same CNN model may generate different results on the same image. By computing the standard deviation of predictions, the region with higher variability could be off higher uncertainty.

The present disclosure may be more computationally efficient than existing methods and can classify, detect, and segment lesions on microscopy images in real time.

The present disclosure fuses findings in different scales for higher accuracy.

The present disclosure generates an uncertainty map and a confidence score to assist interpretation results. Users may refer to the results and also make decisions based on the certainty level of the prediction.

The number of hierarchical levels can be altered based on the need of the application. The network architecture may be modified by adding or reducing convolutional layers. The system may be extended to process other types of medical image data, such as WSIs, computed tomography (CT) images, magnetic resonance images (MRIs), positron emission tomography (PET) images, etc.

The system can be extended to process other types of large image data such as satellite remote sensing images.

As used herein, the term component is intended to be broadly construed as hardware, firmware, or a combination of hardware and software.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method, comprising:
   obtaining an input tissue image having an input resolution;
   down-sampling the input tissue image to a first resolution;
   down-sampling the input tissue image to a second resolution that is between the first resolution and the input resolution of the input tissue image;
   performing a first image analysis at the first resolution of the input tissue image;
   generating a first analysis result and a first uncertainty map based on performing the first image analysis;
   identifying a first set of uncertain regions of the input tissue image based on the first uncertainty map;
   performing a second image analysis of the first set of uncertain regions at the second resolution of the input tissue image;
   generating a second analysis result and a second uncertainty map based on performing the second image analysis;
   generating a final uncertainty map by fusing the first uncertainty map and the second uncertainty map; and
   generating a final analysis result by fusing the first analysis result and the second analysis result.

2. The method of claim 1, wherein the input tissue image is a microscopy image.

3. The method of claim 1, wherein the input tissue image is a whole-slide image.

4. The method of claim 1, wherein the final analysis result includes at least one of a classification of the input tissue image, an object detection of the input tissue image, and a segmentation of the input tissue image.

5. The method of claim 1, wherein the first resolution is a minimal resolution.

6. The method of claim 1, wherein the second image analysis is only performed on the first set of uncertain regions.

7. A device, comprising:
   at least one memory configured to store program code;
   at least one processor configured to read the program code and operate as instructed by the program code, the program code including:
   obtaining code configured to cause the at least one processor to obtain an input tissue image having an input resolution;
   down-sampling code configured to cause the at least one processor to down-sample the input tissue image to a first resolution, and down-sample the input tissue image to a second resolution that is between the first resolution and the input resolution of the input tissue image;
   first performing code configured to cause the at least one processor to perform a first image analysis at the first resolution of the input tissue image;
   first generating code configured to cause the at least one processor to generate a first analysis result and a first uncertainty map based on performing the first image analysis;
   first identifying code configured to cause the at least one processor to identify a first set of uncertain regions of the input tissue image based on the first uncertainty map;
   second performing code configured to cause the at least one processor to perform a second image analysis of the first set of uncertain regions at the second resolution of the input tissue image;
   second generating code configured to cause the at least one processor to generate a second analysis result and a second uncertainty map based on performing the second image analysis;
   third generating code configured to cause the at least one processor to generate a final uncertainty map by fusing the first uncertainty map and the second uncertainty map; and
   fourth generating code configured to cause the at least one processor to generate a final analysis result by fusing the first analysis result and the second analysis result.

8. The device of claim 7, wherein the input tissue image is a microscopy image.

9. The device of claim 7, wherein the input tissue image is a whole-slide image.

10. The device of claim 7, wherein the final analysis result includes at least one of a classification of the input tissue image, an object detection of the input tissue image, and a segmentation of the input tissue image.

11. The device of claim 7, wherein the first resolution is a minimum resolution.

12. The device of claim 7, wherein the second image analysis is only performed on the first set of uncertain regions.

13. A non-transitory computer-readable medium storing instructions, the instructions comprising: one or more instructions that, when executed by one or more processors of a device, cause the one or more processors to:
   obtain an input tissue image having an input resolution;
   down-sample the input tissue image to a first resolution;
   down-sample the input tissue image to a second resolution that is between the first resolution and the input resolution of the input tissue image;
   perform a first image analysis at the first resolution of the input tissue image;
   generate a first analysis result and a first uncertainty map based on performing the first image analysis;
   identify a first set of uncertain regions of the input tissue image based on the first uncertainty map;
   perform a second image analysis of the first set of uncertain regions at the second resolution of the input tissue image;
   generate a second analysis result and a second uncertainty map based on performing the second image analysis;
   generate a final uncertainty map by fusing the first uncertainty map and the second uncertainty map; and
   generate a final analysis result by fusing the first analysis result and the second analysis result.

14. The non-transitory computer-readable medium of claim 13, wherein the input tissue image is a microscopy image.

15. The non-transitory computer-readable medium of claim 13, wherein the input tissue image is a whole-slide image.

16. The non-transitory computer-readable medium of claim 13, wherein the final analysis result includes at least one of a classification of the input tissue image, an object detection of the input tissue image, and a segmentation of the input tissue image.

17. The non-transitory computer-readable medium of claim 13, wherein the second image analysis is only performed on the first set of uncertain regions.

18. The non-transitory computer-readable medium of claim 13, wherein the first resolution is a minimum resolution.

19. The method of claim 1, further comprising:
identifying a second set of uncertain regions of the input tissue image based on the second uncertainty map;
performing a third image analysis of the second set of uncertain regions at the input resolution of the input tissue image;
generating a third analysis result and a third uncertainty map based on performing the second image analysis;
wherein the final uncertainty map is generated by fusing the first uncertainty map, the second uncertainty map, and the third uncertainty map, and
wherein the final analysis result by fusing the first analysis result, the second analysis result, and the third analysis result.

* * * * *